United States Patent [19]

Kuntz

[11] 4,252,132
[45] Feb. 24, 1981

[54] MIDSTREAM URINE SPECIMEN COLLECTING DEVICE

[75] Inventor: David H. Kuntz, Los Angeles, Calif.

[73] Assignee: SHS Enterprises, Ltd., Newport Beach, Calif.

[21] Appl. No.: 949,652

[22] Filed: Oct. 10, 1978

[51] Int. Cl.³ .............................................. A61B 10/00
[52] U.S. Cl. .................................... 128/761; 128/295; 73/215
[58] Field of Search ............... 128/294, 295, 760, 761, 128/762, 766; 73/215; 4/144.1, 144.2, 144.3, 144.4, 301

[56] References Cited

U.S. PATENT DOCUMENTS

| 3,722,503 | 3/1973 | Hovick | 128/761 |
| 3,871,231 | 3/1975 | Ciarico | 73/215 |
| 4,040,791 | 8/1977 | Kuntz | 128/295 |

FOREIGN PATENT DOCUMENTS 2421746  5/1974  Fed. Rep. of Germany ........... 128/295

Primary Examiner—Robert W. Michell
Assistant Examiner—J. L. Krutor
Attorney, Agent, or Firm—Henry M. Bissell

[57] ABSTRACT

A device for collecting a urine specimen, which is particularly adapted for females, is configured and adapted for use while the user is sitting on a toilet in the normal position for voiding. The device selectively collects the clean, contaminant-free mid-stream portion of urine. The device includes a urine specimen container releasably secured to a conduit extending from a collection exit in a urine receiving chamber. This exit is positioned in the chamber above a urine bleed-off exit adapted for removing the first portion of urine at a controlled rate. The collection exit is remote from the bleed-off exit, is shielded from urine splashing thereinto, as by a dome-shaped cap releasably secured thereover, and is below a urine overflow exit in the chamber. The chamber preferably is open topped and is supported on a hollow base within which the specimen container is disposed. An upwardly curved handle extends out from the chamber. The device is inexpensive, simple and disposable and the chamber, base, conduit and handle can be integrally molded in a single operation. The shield and specimen container can be separately formed.

22 Claims, 6 Drawing Figures

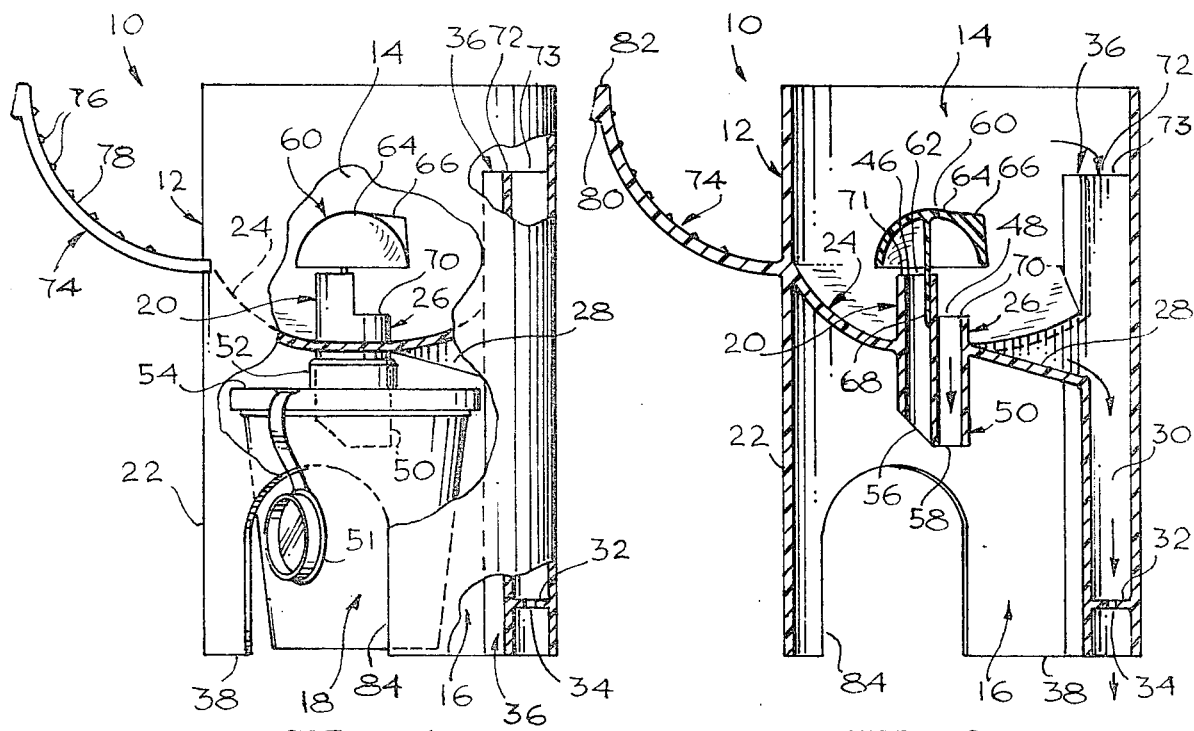
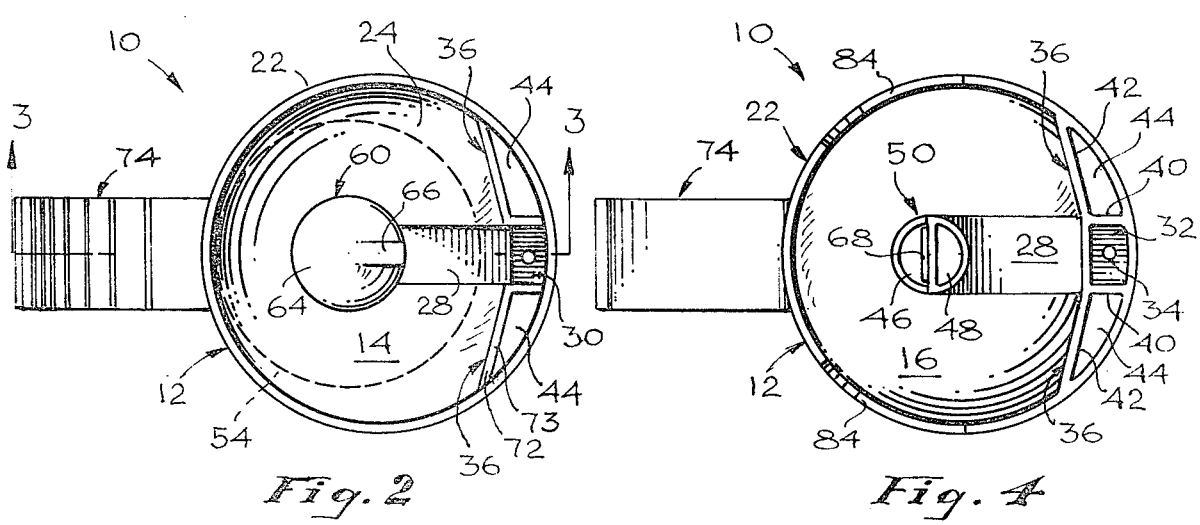
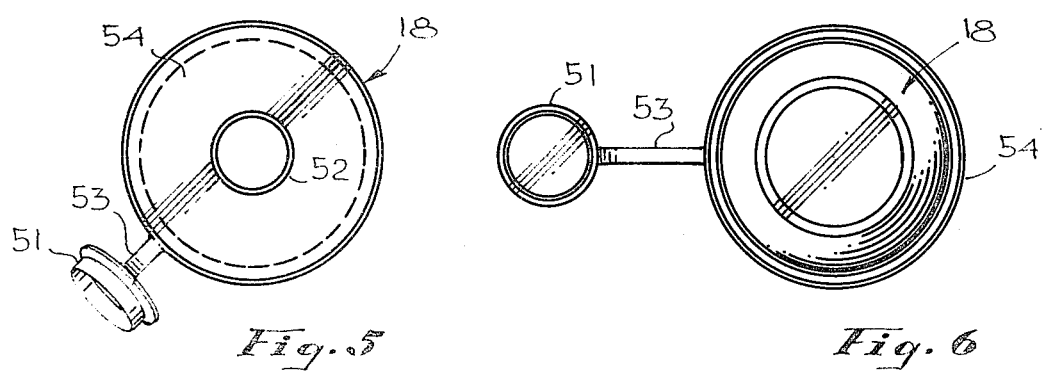
Fig. 1  Fig. 3  Fig. 2  Fig. 4  Fig. 5  Fig. 6

MIDSTREAM URINE SPECIMEN COLLECTING DEVICE

BACKGROUND OF THE INVENTION

1. Field of the Invention

This invention generally relates to collecting devices and, more particularly, to portable urine collection devices, particularly for use by females.

2. Description of the Prior Art

Urine analysis is such a simple, common and useful diagnostic aid that the taking of a urine specimen is generally included in even the simplest of physical examinations. It is important not only as an indicator or detector of certain physical conditions and diseases, but it is also particularly useful in connection with the treatment of infections related to the urinary tract, which are much more common in females than males. However, the problem of collecting a suitable specimen is considerably more complex when a female patient is involved.

Thus, in the collecting of a urine specimen from a female patient, it is important to take the specimen as a "mid-stream" or "clean catch" sample. When a female patient voids in the normal manner, the initial portion is more likely to contain contamination from foreign matter than that portion which follows. This is because the initial portion is expelled with less force and usually is voided as a mere trickle which is likely to trail along the labia and pick up whatever contamination is present in those areas. The mid-stream portion is expelled with the greatest force and is most likely to leave the urethral meatus directly as a stream without contacting the labia or, if it does, the labia will have had most of the contamination washed off by the initial portion.

Some practitioners go to considerable lengths in an effort to obtain an uncontaminated urine sample from a female patient. With the patient in a reclining position, an attendant cleanses the area adjacent the urethral meatus with a suitable solution in an effort to wash off the contamination which is generally present in that area. Even with such precautions, however, contamination may develop in the collected urine sample to a level sufficient to give a false or misleading indication of the bacteria level in the sample. Moreover, taking a sample under such conditions is an extremely awkward and uncomfortable experience for the patient and is fairly costly, since the patient is required to be present in the physician's office or a hospital with a special attendant, usually a nurse, administering the procedure.

What has been needed in some simple but effective, foolproof device, preferably disposable after a single use, which a patient can use with a minimum of instructions and without assistance, while voiding in the normal manner. The device should have the capability of receiving the entire amount of voided urine, rejecting the initial portion, selecting a portion corresponding to the mid-stream sample and transferring it to a specimen container, and rejecting the remainder of the voided urine by directing it, together with any overflow from the specimen container, into the toilet on which the patient is positioned in the normal attitude.

Although the device set forth in U.S. Pat. No. 4,040,791 which issued on Aug. 9, 1977 to applicant of the present application and is entitled Specimen Collecting Device accomplishes the foregoing objects, such device has been found to be somewhat complicated and expensive to manufacuture. For example, it cannot be made in a single high-speed molding operation but must be assembled from a plurality of parts. Moreover, it requires certain close tolerances which demand high quality control. Therefore, it is not as simple and inexpensive as one would desire for a disposable device intended for extensive usage. Moreover, it is somewhat difficult to handle and orient while using it. Therefore, it would be desirable to provide an improved device of the same general type which would be as efficient but less expensive, and easier to handle, orient and use.

SUMMARY OF THE INVENTION

The foregoing objects have been achieved by the improved device of the present invention. The device is substantially as set forth in the Abstract above. Not only is it very simple, but it can be rapidly manufactured into a unitary product in a single low-cost molding operation, preferably from inexpensive material, such as plastic, rubber or the like. Moreover, it is highly efficient in isolating and collecting contaminant-free urine. The device is particularly adapted for convenient use by a female patient while she is sitting on a toilet. Thus, she can void urine into the device and the urine can be easily and simply collected. For such purposes the improved device of the invention comprises a urine-receiving chamber having a urine-receiving opening at its upper end and three urine exits at different levels. The first exit is adjacent the lower end of the chamber and may be in a recess or pocket. It is for bleeding first-voided urine from the chamber and device at a slow controlled rate into the toilet so that as voiding continues the urine level rises to the second exit which is above the first exit and preferably remote therefrom. Thus, the second exit passes clean, contaminant-free mid-stream urine to a detachable urine specimen container positioned therebelow within a hollow support base for the chamber and connected thereto by a conduit. As voiding continues the urine level in the chamber may rise above the second exit, particularly when the specimen container becomes filled. When the urine level reaches the height of the third exit (above the level of the second exit) excess urine passes through that exit and from the chamber and the device to the toilet. Thus, only the clean mid-stream urine is retained in the specimen container. At cessation or diminishing of voiding rate, the excess urine trapped in the chamber below the third exit level bleeds out through the first exit until only the urine sample in the specimen container remains.

An upwardly and outwardly curved handle is preferably disposed on the device on the side opposite the first and third urine exits to facilitate urine run-off into the toilet and correct positioning of the device. The handle may be serrated and have a finger stop. The second exit is preferably centrally located as, for example, in a central vertical stand pipe in the chamber, and a urine-deflecting shield may be releasably attached over the stand pipe and second exit to prevent inadvertent entry of first flow urine into the second exit. Further details of the invention are set forth in the following detailed description and accompanying drawings.

BRIEF DESCRIPTION OF THE DRAWING

FIG. 1 is a schematic side elevation, partly broken away, of a preferred embodiment of the improved urine specimen collecting device of the present invention;

FIG. 2 is a schematic top plan view of the device of FIG. 1;

FIG. 3 is a schematic cross-section, taken along the section line 3—3 of FIG. 2;

FIG. 4 is a schematic bottom plan view of the device of FIG. 1;

FIG. 5 is a schematic top plan view of the specimen container portion of the device of FIG. 1; and FIG. 6 is a schematic bottom plan view of the specimen container portion of the device of FIG. 1.

DESCRIPTION OF THE PREFERRED EMBODIMENT

Now referring more particularly to FIGS. 1–6 of the accompanying drawings, a preferred embodiment of the improved urine specimen collecting device of the present invention is schematically depicted therein. Thus, device 10 is schematically shown in side elevation in FIG. 1. Device 10 includes a generally cylindrical housing 12 comprising an open-topped upper urine-receiving chamber 14 integrally secured to a lower hollow support base 16, and a urine specimen container 18 disposed within base 16 and releasably attached to chamber 14 by a depending conduit 20.

Chamber 14 is defined by the vertical annular side-wall 22 of housing 12 and by a curved closed bottom 24 (FIG. 3). Bottom 24 generally slopes down toward the base of a central vertical hollow stand pipe 26 (FIGS. 1 and 3). However, a ramp portion 28 is provided in bottom 24, which ramp slopes down from the base of standpipe 26 to a generally vertical narrow pocket or recess 30 defined in part by a portion of the periphery (sidewall 22) of device 10. Recess 30 has a generally horizontal wall or bottom 32 adjacent its lower end and the lower end of device 10, which wall 32 defines a narrow vertical urine bleed hole 34 down through which urine exits device 10. Recess 30 is also defined by a pair of spaced, hollow, open-topped vertical columns 36 disposed on opposite sides of recess 30 and which extend to the bottom 38 of device 10 and which also rise above the upper level of standpipe 26 in chamber 14. Columns 36 are each defined by intersecting walls 40 and 42 terminating at side-wall 22 (FIG. 2). Columns 36 define passageways 44 which channel excess urine from chamber 14 and device 10, such urine exiting from the bottom 38 of device 10.

Standpipe 26 comprises a joined pair of hollow open-topped vertical tubes 46 and 48, tube 46 terminating at a higher level than tube 48 above bottom 24 and serving to relieve air from the specimen container 18 as urine enters through the tube 48. Both tuber 46 and 48 terminate well below the top of columns 36. Tubes 46 and 48 depend below chamber 14 and form a dual conduit 50 received within a central opening 52 (FIG. 5) in the removable cover portion 54 of urine specimen container 18 to permit the filling of container 18 from chamber 14. Thus container 18 is slidably releasably received over conduit 50. Preferably, a portion 56 of the lower end 58 of conduit 50 is tapered so that container 18 can be easily slipped on and off conduit 50. A releasable closure 51 is connected to the top of cover 54 via a flexible strip 53 which permits opening 52 to be sealed when container 18 is filled.

A protective urine shield 60 is preferably releasably disposed in the upper end 62 of tube 46. Shield 60 is mushroom shaped. Thus, it comprises a protective dome 64 with an index tab 66 to help align depending blade or stem 68 slidably received in end 62 so that a portion of dome 64 will extend over the open upper ends 70 of tube 48 and 71 of tube 46. It will be noted that stem 68 may be vertically asymmetrically disposed relative to dome 64 to permit dome 64 to extend far enough over to protect ends 70 and 71. Thus, when urine is voided down into chamber 14, dome 64 prevents it from running or splashing directly into ends 70, 71. End 70 forms a urine collection exit which continues as tube 48 of conduit 50.

Thus, it will be noted that chamber 14 is, in part, characterized by the presence of three separate urine exists at different levels: namely, exit 34 at the bottom of recess 30 near bottom 38 of device 10; exit 70 at the top of tube 48 well above the level of exit 34; and exit 72 at the open upper ends 73 of columns 36 well above the level of exit 70. When urine voiding into device 10 is initiated, preferably while the female patient is sitting on a toilet holding device 10 immediately below her urethra, the contaminated first portion of urine passes down into chamber 14, and may strike dome 64 in doing so, but in any event passes down into recess 30 and begins to leave device 10 through exit 34. Since exit 34 is small (preferably about 3/32 inch diameter), urine leaves device 10 slowly enough so that recess 30 becomes filled and, by the time midstream urine is being voided, urine rises to the level of exit 70 in chamber 14 and begins to pass down conduit 50 and into container 18. The urine which passes down conduit 50 is laregly that of the mid-stream portion, so that the urine specimen collected in container 18 is essentially contaminant free. Once container 18 is filled, urine backs up in conduit 50 and the level of urine in chamber 14 rises above exit 70 to the level of overflow exit 72, passes into columns 36 and exits device 10 from bottom 38. Preferably exit 70 is remote from exit 34. Moreover, although exit 34 could theoretically be dispensed with, it is highly desirable in order to remove the most contaminated urine (first flow) immediately from device 10 so as to enhance the purity of the specimen ultimately passed to container 18. It is also useful to empty the collecting chamber 14 after the specimen container 18 is filled.

In order to facilitate holding device 10 conveniently in the right position, a handle 74 is provided which is curved outwardly and upwardly from housing 12 in the area of chamber 14 (FIG. 1) and which preferably terminates at a point level with the top of chamber 14. This is to facilitate molding of handle 74, chamber 14, conduit 50, standpipe 26 and base 16 from rubber, polyethylene, polyvinyl, plastic or the like into a single unitary body in a single, inexpensive, one-step high-speed molding operation. Shield 60 and container 18 can be separately formed in high-speed forming operations from plastic, rubber or the like and thus are also inexpensive. Handle 74 preferably has serrations 76 along the upper surface 78 to facilitate gripping of handle 74 with the user's thumb, and a finger stop 80 adjacent the outer end 82 thereof, again to facilitate gripping of handle 74. This arrangement is symmetrical to facilitate use by both right-handed and left-handed persons. Handle 74 permits device 10 to be easily packaged, stocked and stored, and also to be placed upside down to fit container 18 in place. In addition, base 16 is cut away at a number of spaced locations to provide finger openings 84 to facilitate gripping container 18 while device 10 is in the upright position, for example, in removing a urine filled container 18 from device 10. Closure 51 may also be used to help pull container 18 free of conduit 50, whereupon closure 51 can be secured to opening 52 to seal urine in container 18 against contamination or leakage before testing thereof.

It is preferred to have exits 34 and 72 on the side of device 10 away from (that is, opposite) the handle 74 so that the slight tilt usually given by the patient to device 10 held in the normal position during voiding will help to keep urine flowing from exits 34 and 72 until the chamber 14 is empty.

Thus, device 10 is simple, compact, inexpensive, easy to use and disposable. It can be made from readily available materials at high speed in a single molding operation (except for the optional dome and the container). Moreover, it facilitates the most efficient and rapid collection of contaminant free urine from a female without any mess, inconvenience or embarrassment. Other advantages are as set forth in the foregoing.

Various changes, modifications, alterations and additions can be made in the improved urine specimen collecting device of the present invention and in the components and parameters thereof. All such changes, modifications, alterations and additions as are within the scope of the appended claims form part of the present invention.

What is claimed is:

1. An improved urine specimen collecting device for selectively collecting the mid-stream portion of urine during voiding, said device comprising, in combination:
   (a) a urine specimen container;
   (b) a receiving chamber having an opening for receiving voided urine, a first exit for bleeding urine at a controlled rate from said chamber, a second exit at a level above said first exit for transfer of mid-stream urine to said specimen container, and a third exit at a level above said second exit for draining excess urine from said chamber; and
   (c) a conduit extending directly between said chamber and said specimen container, said conduit communicating with the chamber at said second exit.

2. The improved device of claim 1 wherein said specimen container is releasably connected to said conduit below said second exit, wherein said device is adapted for use by a human female.

3. The improved device of claim 1 wherein said first and second exits are remote from each other.

4. The improved device of claim 1 wherein shielding means is disposed over said second exit to prevent urine from splashing into said second exit.

5. The improved device of claim 1 wherein said device is disposable and includes a hollow open bottom base support below said chamber within which support said specimen container is releasably connected to said conduit, wherein said chamber has an open upper end, and wherein said base support, chamber and conduit are integrally molded together.

6. The improved device of claim 5 wherein said device includes an upwardly curved, ridged handle peripheral of and attached to said chamber, and integrally molded therewith.

7. The improved device of claim 6 wherein said device includes a removable urine shield over said second exit.

8. The improved device of claim 1 wherein the third exit comprises a pair of open passages extending along an inner wall of the device on opposite sides of the first exit.

9. An improved urine specimen collecting device for selectively collecting the mid-stream portion of urine during voiding, said device comprising, in combination:
   (a) a urine specimen container;
   (b) a receiving chamber having an opening for receiving voided urine, a first exit for bleeding urine at a controlled rate from said chamber, a second exit at a level above said first exit for transfer of mid-stream urine to said specimen container, and a third exit at a level above said second exit for draining excess urine from said chamber;
   (c) a conduit extending from said second exit to adjacent said specimen container; and
   (d) shielding means disposed over said second exit to prevent urine from splashing into said second exit; wherein said second exit is disposed in a standpipe and wherein said shielding means is releasably disposed over said standpipe.

10. The improved device of claim 9 wherein said standpipe and conduit are vertically aligned along the center line of said device and wherein said specimen container is releasably connected to the lower end of said conduit below said standpipe.

11. The improved device of claim 10 wherein said first exit is disposed in a recess adjacent the lower end of said chamber at the periphery thereof.

12. The improved device of claim 11 wherein said third exit is disposed adjacent the periphery of said chamber, and wherein said chamber is open-topped and disposed in the upper end of said device on a hollow support base.

13. The improved device of claim 11 wherein said support base has an open lower end within which said specimen container is disposed.

14. The improved device of claim 13 wherein said support base is cut away at a plurality of spaced locations to define finger grip access to the specimen container therein.

15. The improved device of claim 10 wherein said lower end of said conduit is tapered to facilitate said releasable connection with said specimen container and wherein said specimen container includes a removable lid with an opening adapted to releasably receive said conduit lower end, and further includes a releasable closure for said opening.

16. The improved device of claim 9 wherein said shielding means is generally mushroom shaped with a protective dome and a depending blade, the latter releasably received in the upper end of said standpipe.

17. The improved device of claim 16 wherein said upper end of said standpipe is open and wherein said protective dome includes an index tab for rapid alignment of said blade with said standpipe.

18. The improved device of claim 9 wherein said standpipe further includes an additional conduit for releasing air from the specimen container as the container is filling with urine 19. The improved device of claim 18 wherein the additional conduit extends above said second exit but terminates below the shielding means.

20. An improved urine specimen collecting device for selectively collecting the mid-stream portion of urine during voiding, said device comprising, in combination:
   (a) a urine specimen container;
   (b) a receiving chamber having an opening for receiving voided urine, a first exit for bleeding urine at a controlled rate from said chamber, a second exit at a level above said first exit for transfer of mid-stream urine to said specimen container, and a third exit at a level above said second exit for draining excess urine from said chamber; and (c) a conduit extending from said second exit to adjacent said specimen container;

wherein said device includes a handle curving upwardly and outwardly form the periphery of said chamber.

21. The improved device of claim 20 wherein at least one major surface of said handle is ridged to facilitate gripping, and said handle includes a finger stop adjacent the outer end thereof, and wherein the upper end of said handle terminates at the level of the upper end of said chamber to facilitate molding of said device and inverted loading of the specimen container in said device.

22. The improved device of claim 20 wherein said first and third exits are disposed on the side of said chamber opposite from said handle to facilitate urine run-off for emptying the chamber of urine after the selected specimen is in the container.

* * * * *